(12) United States Patent
Kim

(10) Patent No.: US 9,128,095 B2
(45) Date of Patent: Sep. 8, 2015

(54) DIAGNOSIS OR PROGNOSIS OF LUNG CANCER AND COLORECTAL CANCER BASED ON EXPRESSION LEVEL OF GLUTAREDOXIN 3

(75) Inventor: Il Han Kim, Daejeon (KR)

(73) Assignee: PAICHI UNIVERSITY INDUSTRY-ACADEMIC COOPERATION FOUNDATION, Daejeon (KR)

( * ) Notice: Subject to any disclaimer, the term of this patent is extended or adjusted under 35 U.S.C. 154(b) by 1019 days.

(21) Appl. No.: 13/259,918

(22) PCT Filed: Apr. 15, 2009

(86) PCT No.: PCT/KR2009/001945
§ 371 (c)(1),
(2), (4) Date: Sep. 23, 2011

(87) PCT Pub. No.: WO2010/123159
PCT Pub. Date: Oct. 28, 2010

(65) Prior Publication Data
US 2012/0015847 A1  Jan. 19, 2012

(30) Foreign Application Priority Data
Apr. 8, 2009 (KR) .......... 10-2009-0030364

(51) Int. Cl.
| | | |
|---|---|---|
| G01N 1/00 | (2006.01) | |
| G01N 33/00 | (2006.01) | |
| G01N 33/48 | (2006.01) | |
| G01N 33/50 | (2006.01) | |
| G01N 33/53 | (2006.01) | |
| G01N 33/574 | (2006.01) | |
| C12N 9/02 | (2006.01) | |

(52) U.S. Cl.
CPC ........ *G01N 33/57423* (2013.01); *C12N 9/0004* (2013.01); *C12Y 120/04001* (2013.01); *G01N 33/57419* (2013.01); *G01N 2333/902* (2013.01)

(58) Field of Classification Search
CPC ......... G01N 1/00; G01N 33/00; G01N 33/48; G01N 33/50; G01N 33/5005; G01N 33/5008; G01N 33/5011; G01N 33/502; G01N 33/5041; G01N 33/53; G01N 33/574; G01N 33/57407; G01N 33/57423; G01N 2201/00; G01N 2333/00; G01N 2333/90; G01N 2333/902; C12N 1/00; C12N 9/00; C12N 9/0004; A61K 6/00; A61K 31/00; A61K 31/33
See application file for complete search history.

(56) References Cited

U.S. PATENT DOCUMENTS
2005/0272052 A1  12/2005  Shekar et al.
2008/0050332 A1  2/2008  Sivak FOREIGN PATENT DOCUMENTS
| WO | 00/36083 A2 | 6/2000 |
| WO | 2004/022778 A1 | 3/2004 |
| WO | 2008/154012 A2 | 12/2008 |

OTHER PUBLICATIONS

Ohayon et al. Journal of Histochemistry & Cytochemistry. 58(9): 799-806, 2010.*
Kato et al. Cellular Immunology 251: 62-67, May 13, 2008.*
NCBI Gene information, 9 pages, Feb. 1, 2015.*
Le et al. Biochemistry 51(9): 1687-1696, Feb. 28, 2015.*
Lu et al. (Proteomics 8: 2220-2229, published online Jun. 5, 2008).*
Information Hyperlinked over Proteins, Feb. 5, 2015.*
Lillig, C.H. et al., "Gluxaredoxin systems," Nov. 2008, Biochimica et Biophysica Acta, vol. 1780, No. 11, pp. 1304-1317.
International Search Report dated May 10, 2010 of PCT/KR2009/001945 which is the parent application—6 pages.
Steiner et al., "Serial Analysis of Gene Expression Reveals Picot is Overexpressed in Patients with Poor Prognosis Malignant Pleural Mesothelioma", Association for Academic Surgery and Society of University Surgeons, Jan. 25, 2007, pp. 164-165.
Witte et al., "INhibition of the c-Jun N-terminal Kinase/AP-1 and Nf-kB Pathway by PICTO, a Novel Protein Kinase C-interacting Protein with a Thioredoxin Homology Domain", The Journal of Biological Chemistry, 2000, vol. 275, No. 3, pp. 1902-1909.
Cha et al., "Preferential overexpression of glutaredoxin3 in human colon and lung carcinoma", Cancer Epidemiology, 2009, vol. 33, pp. 281-287.
European Search Report dated Feb. 8, 2013 of corresponding European Patent Application No. 09843687.6—8 pages.

* cited by examiner

*Primary Examiner* — Alana Harris Dent
(74) *Attorney, Agent, or Firm* — Knobbe, Martens, Olson & Bear, LLP (57) ABSTRACT

The present invention relates to a biomarker for diagnosing lung cancer and colorectal cancer containing glutaredoxin 3 as an active ingredient, and a kit for diagnosing lung cancer and colorectal cancer using the same biomarker. Glutaredoxin 3 of the present invention is over-expressed in lung cancer tissue and colorectal cancer tissue, which enables early prediction of diagnosis or prognosis of lung cancer and colorectal cancer. Thus, glutaredoxin 3 can be helpfully used as a biomarker for diagnosing lung cancer and colorectal cancer.

6 Claims, 6 Drawing Sheets

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
```

<223> OTHER INFORMATION: Forward primer for Glrx 1

<400> SEQUENCE: 1
tcagtcaatt gcccatcaaa                                               20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for Glrx 1

<400> SEQUENCE: 2
cagcagttcc ccactctgtt                                               20

<210> SEQ ID NO 3
<211> LENGTH: 20
<212> TYPE: DNA
<213> ORGANISM: Artificial Sequence
<220> FEATURE:
<223> OTHER INFORMATION: Forward primer for Glrx 2

<400> SEQUENCE: 3
ctgggatgga gagcaataca                                               20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for Glrx 2

<400> SEQUENCE: 4
caggtccagt tccaccactt                                               20

<210> SEQ ID NO 5
<211> LENGTH: 20
<212> TYPE: DNA
<213> ORGANISM: Artificial Sequence
<220> FEATURE:
<223> OTHER INFORMATION: Forward primer for Glrx 3

<400> SEQUENCE: 5
aaagccaagt ccctccttgt                                               20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for Glrx 3

<400> SEQUENCE: 6
gcatgtgcac catctaatcg                                               20

<210> SEQ ID NO 7
<211> LENGTH: 20
<212> TYPE: DNA
<213> ORGANISM: Artificial Sequence
<220> FEATURE:
<223> OTHER INFORMATION: Forward primer for Glrx 5

<400> SEQUENCE: 7
gctggtgaag aaggacaagg                                               20

```
<210> SEQ ID NO 8
<211> LENGTH: 20
<212> TYPE: DNA
<213> ORGANISM: Artificial Sequence
<220> FEATURE:
<223> OTHER INFORMATION: Reverse primer for Glrx 5

<400> SEQUENCE: 8
tcgccattga ggtacacttg                                              20

<210> SEQ ID NO 9
<211> LENGTH: 20
<212> TYPE: DNA
<213> ORGANISM: Artificial Sequence
<220> FEATURE:
<223> OTHER INFORMATION: Forward primer for Survivin

<400> SEQUENCE: 9
gacgacccca tagaggaaca                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for Survivin

<400> SEQUENCE: 10
tccgcagttt cctcaaattc                                              20
```

DIAGNOSIS OR PROGNOSIS OF LUNG CANCER AND COLORECTAL CANCER BASED ON EXPRESSION LEVEL OF GLUTAREDOXIN 3

TECHNICAL FIELD

The present invention relates to a diagnostic biomarker for lung cancer and colorectal cancer, comprising glutaredoxin 3 as an active ingredient, and a diagnostic kit for lung cancer and colorectal cancer, using the same biomarker.

BACKGROUND ART

With the increase in the smoking population and the aggravation of air pollution, lung cancer cases have rapidly increased in South Korea. A Korean statistical report has it that lung cancer cases rank first after stomach cancer in men and come after breast cancer, uterine cancer, stomach cancer and colorectal cancer in women, and is associated with the highest mortality in both men and women. The frequency of incidence of lung cancer and the mortality rate from lung cancer in Korea are expected to increase for a significant period of time in the future in light of the current trend of the smoking rate.

There are two major cell types of lung cancer, small cell lung carcinoma and non-small cell lung carcinoma. Non-small cell lung carcinoma accounts for about 80% of lung cancer cases and is further divided into the three main subtypes of adenocarcinoma, squamous cell carcinoma and large cell carcinoma.

As the cells grow, the lung cancer causes various symptoms including vascular invasion into adjacent tissues, airway blockage, metastasis to lymph nodes, etc. Approximately 10~15% of lung cancer cases without any symptoms are diagnosed during a regular checkup. In most cases, lung cancer, when diagnosed, has already progressed to stage III or beyond, so that they are, for the most part, difficult to cure. Therefore, early diagnosis of lung cancer is presenting itself as an urgent problem to be solved so that the mortality from lung cancer can be reduced.

Various methods are used in combination to diagnose lung cancer. So far, a number of lung cancer screening tests have been employed, including examination of tumor size, metastasis to lymph nodes, immunohistochemistry of biopsy samples of tumerified lung tissue or lymph nodes, chest X-ray screening, chest computerized tomography, and bronchoscopy. Lung cancer can be shown in chest computerized tomography only if the size of the tumor is 0.1 cm or larger. However, lung cancer with this size has probably already metastasized to other tissues. In bronchoscopy, the inside of the lung can be directly observed with an endoscope, but there is the problem of spatial limitation that makes it difficult to observe tumors in deep places.

To supplement such lung cancer screening methods, attempts have been made to use the levels of CBC (complete blood count), serum electrolytes (including calcium), alkaline phosphatase, albumin, AST (aspartate aminotransferase), ALT (alanine transaminase), total bilirubin or creatinine, to diagnose breast cancer. Although their potential values as diagnosis or prognosis factors, the application of conventional tumor biomarkers has shown limit in specificity and sensitivity, and there are no officially recommended breast cancer markers.

The most common cell type of colorectal cancer is adenocarcinoma from the view of pathology. Colorectal cancer is broadly divided into colon cancer and rectal cancer depending on the site of the lesion. As high as about 50% of colorectal cancer cases occur in the lower tract of the large intestine, that is, the rectum. Recent research data indicate that the incidence of colorectal cancer and the mortality from colorectal cancer have significantly increased in Korea, with the westernization of dietary habits. Risk factors for colorectal cancer, although remaining unclear, include heredity, dietary habits associated with the intake of high-fat and low-fiber diet, and inflammatory bowel disease.

Colorectal cancer may attack persons of all ages, but the risk of developing colorectal cancer increases with age and most cases occur in patients in their 60s and 70s. Colon cancer occurs at a relatively higher rate in women than in men, but in the case of rectal cancer, the reverse is true.

To treat colorectal cancer, colectomy is predominantly used in combination with chemotherapy and radiotherapy. In spite of advances in surgical therapy, chemotherapy and radiotherapy, the mortality from colorectal cancer is high because colorectal cancer is caught at too late of a stage for it to be surgically operated on in many cases because the cancer progresses without any particular symptoms. Colorectal cancer patients have an average 5-year survival of approximately 90% or higher for stage I, approximately 70% or higher for stage II, and approximately 50% for stage III whereas the average 5-year survival decreases to approximately 5% in the case of stage IV (2004 Information on Cancer, published by the National Cancer Center, Korea). When colorectal cancer is detected in the earlier stages, it is more likely to be curable, resulting in a greater increase in survival rate.

Screening for colorectal cancer is recommended in individuals who are at high risk. There are several different tests available for this purpose, including rectal digital examination, fecal occult blood test and colonography. The earliest detection procedures presently available for, colorectal cancer involve using tests for fecal blood or endoscopic procedures. However, the size of the tumor must be significant before fecal blood is detected. The sensitivity of the guaiac-based fecal occult blood tests is as low as approximately 26%, which means the 74% of patients with malignant lesions will remain undetected. The visualization of precancerous and cancerous lesions represents the best approach to early detection, but colonoscopy is invasive and accompanied by significant costs, risks, and complications.

Such conventional methods suffer from the disadvantages of having poor accuracy in diagnosis, being unable to diagnose colorectal cancer in its pre-stages and being unable to predict the onset of colorectal cancer, and inconveniencing patients. As a supplement for such conventional colorectum screening methods, attempts have been made to use blood tumor marker levels to diagnose colorectal cancer.

At present, primarily diagnostic blood tests based on the detection of carcinoembryonic antigen (CEA), a tumor-associated glycoprotein, are available to assist with diagnosis in the field of colorectal cancer. Carcinoembryonic antigen is increased in 95% of tissue samples obtained from patients with colorectal, gastric, and pancreatic cancers and in the majority of breast, lung, and head and neck carcinomas. Elevated carcinoembryonic antigen levels have also been reported in patients with non-malignant disease, and many patients with colorectal cancer have normal CEA levels in the serum, especially during the early stage of the disease. The utility of carcinoembryonic antigen as measured from serum or plasma in detecting recurrences is reportedly controversial and has yet to be widely applied.

Therefore, there is long lasting unmet need for a biomarker that allows lung cancer and colorectal cancer to be accurately diagnosed in their early stages and which improves the chance of survival for the patients.

Glutaredoxins (Glrx) are small redox enzymes of approximately 100 amino acid residues that use reduced glutathione as a cofactor in reducing various substrates by a dithiol-monothiol mechanism. There are two main groups of glutaredoxins divided into dithiol glutaredoxins with the characteristic active site consensus sequence Cys-Pro-Tyr-Cys and monothiol glutaredoxins with a Cys-Gly-Phe-Ser active site consensus sequence which lacks one C-terminal active site thiol. Monothiol glutaredoxins can be further categorized into single domain monothiol glutaredoxins and multi-domain glutaredoxins. The single domain monothiol glutaredoxins consist of only one glutaredoxin domain while the multi-domain monothiol glutaredoxins contain an N-terminal thioredoxin-like domain and one to three C-terminal monothiol glutaredoxin domains. The multi-domain monothiol glutaredoxins are restricted to eukaryotic cells while dithiol glutaredoxins and single domain monothiol glutaredoxins are common to all living organisms.

Glutaredoxins are divided into glutaredoxin 1, glutaredoxin 2 glutaredoxin 3 and glutaredoxin 5 . Human glutaredoxin 1 and glutaredoxin 2 are respectively cytosolic and mitochondrial isoforms. Human glutaredoxin 3 is a multi-domain monothiol glutaredoxin and human glutaredoxin 5 is a single domain monothiol glutaredoxin located in the mitochondria.

Cellular redox states are associated with major cellular processes including differentiation, transformation, and apoptosis. Human glutaredoxin 1 binds to mitogen-activated protein kinase kinase kinase 5 (MAP3K5 also known as apoptosis signal-regulating kinase 1) dependent on its redox status. In this complex, the kinase activity of MAP3K5 is suppressed. Oxidation of glutaredoxins leads to the dissociation of the complex and the activation of MAP3K5. Hence, glutaredoxin 1 may regulate MAP3K5's kinase activity in response to the glutathione redox state. In addition, glutaredoxin 1 protects cells from hydrogen peroxide-induced apoptosis by regulating the redox state of protein kinase B.

Glutaredoxin 2 protects HeLa cells from oxidative stress-induced apoptosis.

Glutaredoxin3 was identified as a protein kinase C theta (PRKCQ)-interacting protein that inhibits the activation of mitogen-activated protein kinase 8 (MAPK8 also known as c-Jun N-terminal kinase) stimulated with PMA (phorbol myristate acetate), ultraviolet radiation, or transcription factors jun oncogene (JUN, also known as AP-1) and NF-κB (nuclear factor kappa-B) in Jurkat T cells. In a subsequent study, the treatment of Jurkat T cells with hydrogen peroxide induced the tyrosine phosphorylation of glutaredoxin 3 in a dose-dependent manner that was also dependent on LCK (lymphocytespecific protein tyrosine kinase). MAP3K5 activates the MAPK8 and MAPK14 pathways and is required for tumor necrosis factor α-induced apoptosis. These observations suggest that glutaredoxin 3 inhibits apoptosis via its role in cell activation-associated signaling pathways or in the cellular response to stress signals.

Thus, these data indicate the involvement of glutaredoxins in the process of oncogenesis. However, only a few studies report the association of glutaredoxin 1 with cancer. Overexpression of glutaredoxin 1 was found to increase the resistance of MCF7 breast cancer cells to doxorubicin, a widely used anti-cancer agent. An immunohistochemical analysis by Nakamura et al. revealed increased expression of glutaredoxin 1 in cancerous pancreatic tissue.

As mentioned above, there are reports on the association of glutaredoxin 1 with carcinogenesis, but the association of glutaredoxin 3 with cancer has been little studied. In fact, almost no studies have been done on the use of glutaredoxin 3 as a diagnostic biomarker for cancer, especially lung cancer and colorectal cancer. In this invention, glutaredoxin 3 is used as a diagnostic biomarker for lung cancer and colorectal cancer that allows the accurate early diagnosis and prognosis of lung cancer and colorectal cancer.

DISCLOSURE

Technical Problem

Leading to the present invention, intensive and thorough research into a diagnostic biomarker for lung cancer and colorectal cancer, conducted by the present inventors, resulted in the finding that glutaredoxin 3 is highly expressed in cancerous tissues of the lung and the colon, but not expressed in normal tissues in those organs.

TECHNICAL SOLUTION

The present invention aims to provide a diagnostic biomarker for lung cancer and colorectal cancer, comprising glutaredoxin 3 as an active ingredient, and a diagnostic kit for lung cancer and colorectal cancer using the same biomarker.

BEST MODE

In accordance with an aspect thereof, the present invention provides a diagnostic biomarker for lung cancer and colorectal cancer, comprising glutaredoxin 3 as an active ingredient.

In accordance with another aspect thereof, the present invention provides a diagnostic biomarker for lung cancer and colorectal cancer, comprising an antibody against glutaredoxin 3.

In accordance with a further aspect thereof, the present invention provides a method for detecting glutaredoxin 3 in the lung and the colon through the antigen-antibody reaction using the antibody specifically binding to glutaredoxin 3, used as a biomarker for lung cancer and colorectal cancer.

Below, a detailed description will be given of the present invention.

In the present invention, the expression levels of glutaredoxin 3 was identified to be the highest in lung cancer and colorectal cancer tissues among the 8 solid cancer tissues as measured by qRT-PCR and Western blotting. Found to be overexpressed in lung cancer and colorectal cancer tissues, glutaredoxin 3 allows the diagnosis and prognosis of lung cancer and colorectal cancer and thus is useful as a diagnostic biomarker for the diseases.

The diagnostic kit for lung cancer and colorectal cancer, comprising an antibody against glutaredoxin 3 in accordance with the present invention may be readily prepared by a method known in the art using the biomarker.

The diagnostic kit for lung cancer and colorectal cancer of the present invention may comprise an antibody specifically binding to glutaredoxin 3 a secondary antibody conjugate with a label that can react with a substrate to cause a chromatic change, a substrate solution which develops a color upon reaction with the label, a washing buffer and a reaction stop buffer.

Preferably, the label conjugated to the secondary antibody is preferably a coloring agent which can bring about a color change as it reacts with its substrate. Representative among them are HRP (horseradish peroxidase), alkaline phosphatase, colloid gold, fluorescein such as FITC (poly L-lysine-fluorescein isothiocyanate) and RITC (rhodamine-B-isothiocyanate), and a dye.

As for the substrate solution, it is dependent on the label. Examples include TMB (3,3',5,5'-tetramethyl bezidine), ABTS [2,2'-azino-bis(3-ethylbenzothiazoline-6-sulfonic acid)], and OPD (o-phenylenediamine). The coloring substrate is preferably provided in the form of a solution in a buffer (0.1M NaOAc, pH 5.5).

Preferably, the washing solution may contain phosphate buffer, NaCl and Tween 20. More preferable is a solution (PBST) containing 0.02 M phosphate buffered saline, 0.13 M NaCl, and 0.05% Tween 20. After the antibody is allowed to react with the antigen, the antigen-antibody complex is treated with the secondary antibody conjugate, followed by immobilization and then washing three to six times with the washing solution. A sulfuric acid solution may be used to stop the enzymatic reaction.

In accordance with one embodiment of the present invention, the diagnosis or prognosis of early lung cancer and colorectal cancer can be predicted with high accuracy by detecting the cancer biomarker glutaredoxin 3 with an antigen-antibody reaction using an antibody specifically binding to glutaredoxin 3. For example, a protein preparation containing glutaredoxin 3 is separated by SDS-PAGE, and transferred and fixed onto an immobilizer which is then treated with an antibody against glutaredoxin 3 to determine the protein level of glutaredoxin 3. That is, when the protein level of glutaredoxin 3 in the lung or colon tissue of interest is measured, the lung or colon tissue is diagnosed with cancer or predicted to become cancerous when the glutaredoxin 3 expression level is higher than that of normal lung or colon tissue.

Higher expression levels of glutaredoxin 3 are detected in stage I-IV lung cancer or colorectal cancer tissues than in normal lung or colon tissue.

As the immobilizer, a nitrocellulose membrane, a PVDF (polyvinylidene difluoride) membrane, a 96-well plate formed of polyvinyl resin or polystyrene resin, or a slide glass may be used.

The antigen-antibody binding reaction may be assayed using a typical method such as enzyme-linked immunosorbent assay (ELISA), radioimmunoassay (RIA), sandwich assay, Western blotting, immunoprecipitation immunohistochemical staining, immunofluorescence assay, enzyme-substrate coloring assay, and antigen-antibody aggregation.

Mode For Invention

A better understanding of the present invention may be obtained from the following examples which are set forth to illustrate, but are not to be construed as limiting the present invention.

EXAMPLE 1 qRT-PCR Assay qRT-PCR (Quantitative real-time Polymerase Chain Reaction) was performed to characterize the expression profile of human target genes by using the human qRT-PCR arrays.

Expression levels of target genes in different cancers were measured using the Cancer Survey real-time quantitative PCR arrays (CSRT 96-I array) and specific cancer-focused Tissue qPCR Arrays from OriGene (OriGene Technologies Inc., Rockville, Md., USA). The' CSRT 96-I array consisted of 12 samples (n=3 for normal, n=9 for corresponding cancer) from different individuals for each of eight types of cancer (breast, colon, kidney, liver, lung, ovary, prostate, and thyroid) with cancer stages from I to IV, for a total of 96 samples. The specific cancer-focused Tissue qPCR Arrays used in this experiment are summarized in Table 1. More clinicopathological information for each patient is described in OriGene's product sheet.

TABLE 1

| Cancerous Tissue | Array Name | No. of Sample ||||| N/A (not determined) |
| --- | --- | --- | --- | --- | --- | --- | --- |
| | | 0 (Normal) | I | II | III | IV | |
| Bladder | BLRT | 4 | 3 | 5 | 8 | 4 | — |
| Breast | BCRT II | 7 | 10 | 20 | 11 | — | — |
| Colon | HCRT II | 5 | 10 | 13 | 14 | 6 | — |
| Kidney | HKRT | 7 | 21 | 6 | 8 | 6 | — |
| Liver | LVRT | 8 | 7 | 8 | 8 | 3 | — |
| Lung | HLRT II | 5 | 25 | 6 | 10 | 2 | 1 |
| Lymphoma | LYRT | 6 | 32 | 6 | — | 4 | — |
| Ovary | HORT IV | 6 | 7 | 1 | 33 | 1 | — |
| Prostate | HPRT II | 8 | — | 22 | 11 | 2 | — |
| Thyroid | HTRT | 5 | 16 | 6 | 16 | 5 | 5 |

PCR was performed in 96-well optical plates using iCycler (Bio-Rad Laboratories, Hercules, Calif., USA) with primers specific for Glrx 1 Glrx 2 Glrx 3 Glrx 5 survivin, β-actin, and GAPDH (glyceraldehyde 3-phosphate dehydrogenase), and iQ SYBR Green Supermix (Bio-Rad). The resulting fluorescence proportional to the amount of amplified DNA was measured at 530 nm at the end of each elongation phase. A standard graph of $C_T$ (the point at which the fluorescence crosses the threshold) values obtained from serially diluted target genes was constructed for all reactions so as to ensure that they were amplified and reported in proportion to the template. $C_T$ values were converted to gene copy number of the template complementary DNA (cDNA) using the equation $2^{\Delta\Delta C_T}$. The $\Delta C_T$ is the abundance of cDNAs for transcripts of each gene normalized to the β-actin or GAPDH at each time. The $\Delta\Delta C_T$ is obtained by subtracting a calibrator value for each gene transcript being assayed. In parallel with each cDNA sample, standard curves were generated to correlate CT values using serial dilutions of the target gene. The quality of the standard curve was judged from the slope and correlation coefficient. Quantification was performed by comparing the fluorescence of a PCR product of unknown concentration with the fluorescence of several dilutions. Melting curve analysis was used for product validation. The primers for β-actin and GAPDH were supplied by OriGene. Other primer sequences are summarized in Table 2.

TABLE 2

| Primer for RT-PCR Amplification | Primer Direction | Sequence (5'->3') |
|---|---|---|
| Glrx 1 | Forward | tcagtcaattgcccatcaaa (SEQ ID NO: 1) |
|  | Reverse | cagcagttccccactctgtt (SEQ ID NO: 2) |
| Glrx 2 | Forward | ctgggatggagagcaataca (SEQ ID NO: 3) |
|  | Reverse | caggtccagttccaccactt (SEQ ID NO: 4) |
| Glrx 3 | Forward | aaagccaagtccctccttgt (SEQ ID NO: 5) |
|  | Reverse | gcatgtgcaccatctaatcg (SEQ ID NO: 6) |
| Glrx 5 | Forward | gctggtgaagaaggacaagg (SEQ ID NO: 7) |
|  | Reverse | tcgccattgaggtacacttg (SEQ ID NO: 8) |
| Survivin | Forward | gacgaccccatagaggaaca (SEQ ID NO: 9) |
|  | Reverse | tccgcagtttcctcaaattc (SEQ ID NO: 10) |

1-1 . mRNA Expression Levels of Glutaredoxin 1, 2, 3 and 5 in Tissues of 8 Solid Cancers The mRNA expression levels of glutaredoxin in tissues of 8 solid cancers (breast, colon, kidney, liver, lung, ovary, prostate and thyroid) were measured using cancer-focused tissue qRT-PCR arrays. For each type of the eight cancers, 12 samples (normal tissues n=3 cancerous tissues (stage I~IV) n=9) from different individuals were used.

Figure 1:
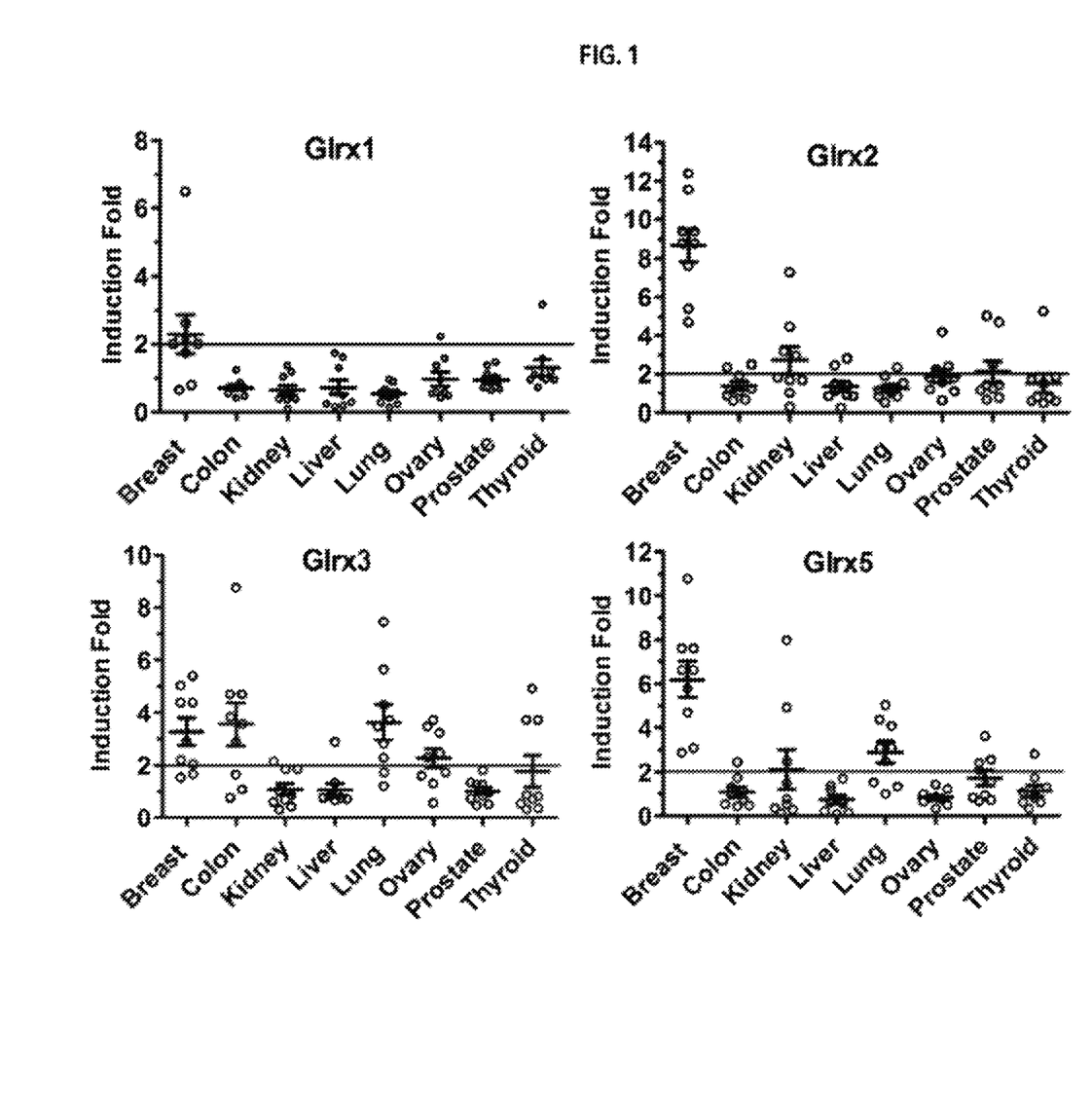
FIG. 1 is of graphs showing expression profiles of glutaredoxin 1, 2, 3, 5 mRNA in 8 different solid cancers (breast, colon, kidney, liver, lung, ovary, prostate and thyroid) as measured by qRT-PCR.

The results are given in FIG. 1.

As can be seen in FIG. 1, the mRNA expression levels of glutaredoxin 1, 2, 3 and 5 were elevated in the breast cancer tissue samples higher than they were in the seven solid cancers. On the other hand, the mRNA level of glutaredoxin 3 was found to increase many times in tissue samples of lung cancer and colorectal cancer (lung: 3.6 times, colon: 3.7 times).

1-2 . mRNA Expression Levels of Glutaredoxin 1, 2, 3 and 5 in Lung Cancer Tissue For mRNA expression profiling of glutaredoxin 1, 2, 3 and 5 in lung cancer tissues, the HLRT II array was used to determine the transcript levels of glutaredoxin 1, 2, 3 and 5, and the induction folds were obtained from the mRNA levels. The HLRT II array was comprised of 5 samples of normal lung tissue and 43 samples of lung cancer tissues from different individuals.

Figure 2:
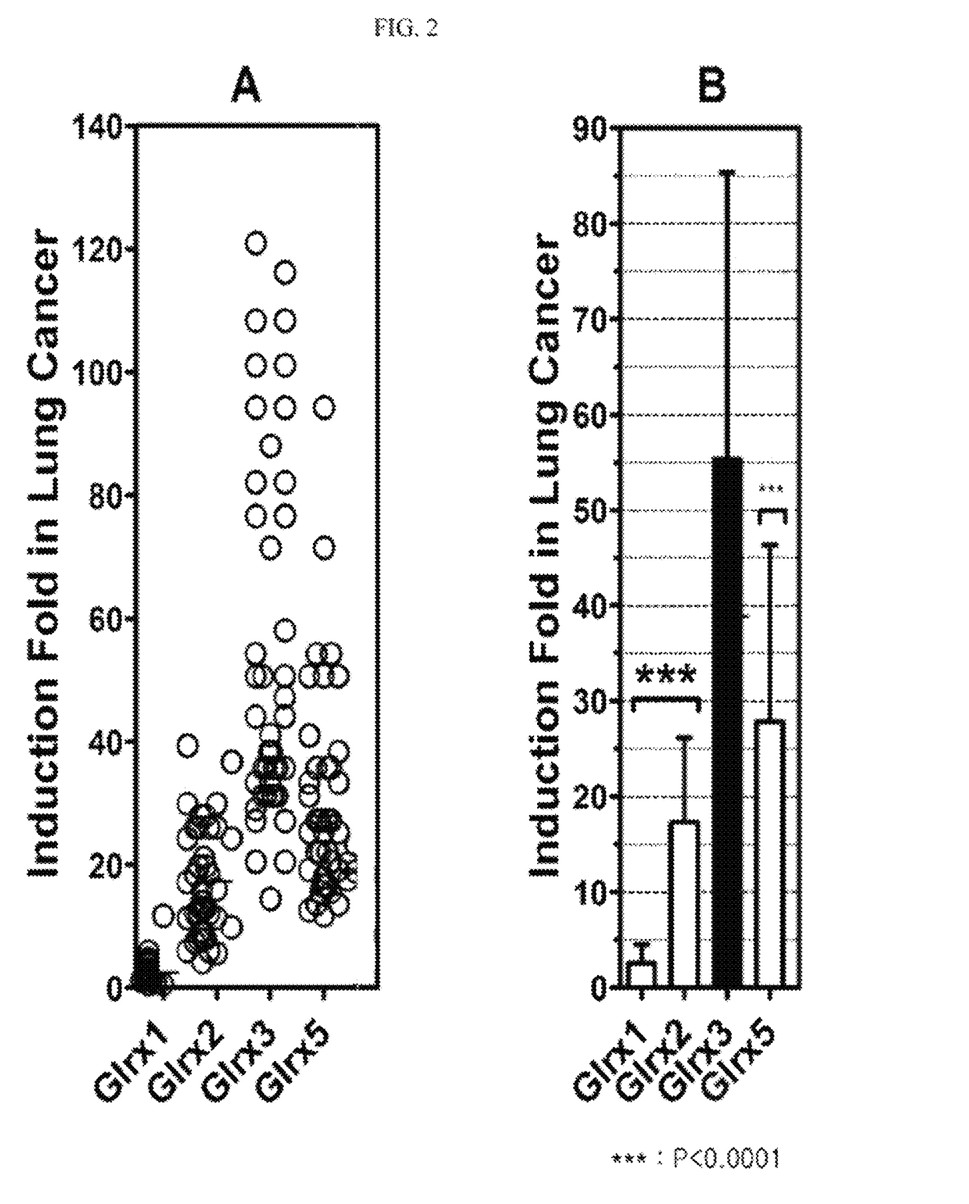
FIGS. 2A and 2B are of graphs showing mRNA levels of glutaredoxin 1, 2, 3 and 5 in lung cancer as measured by qRT-PCR using HLRT II arays, and magnitudes of induction fold obtained therefrom.

The results are given in FIGS. 2A and 2B.

As is apparent from the data of FIGS. 2A and 2B, the mRNA level of glutaredoxin 3 was the highest in lung cancer tissues (induction fold, 55.3 ±31.0 ).

1-3 . mRNA Expression Levels of Glutaredoxin 1, 2, 3 and 5 in Colorectal Cancer Tissue For mRNA expression profiling of glutaredoxin 1, 2, 3 and 5 in colorectal cancer tissues, the HCRT II array was used to determine the transcript levels of glutaredoxin 1, 2, 3 and 5, and induction folds were obtained from the mRNA levels. The HCRT II array was comprised of 5 samples of normal lung tissue and 43 samples of lung cancer tissues from different individuals.

Figure 3:
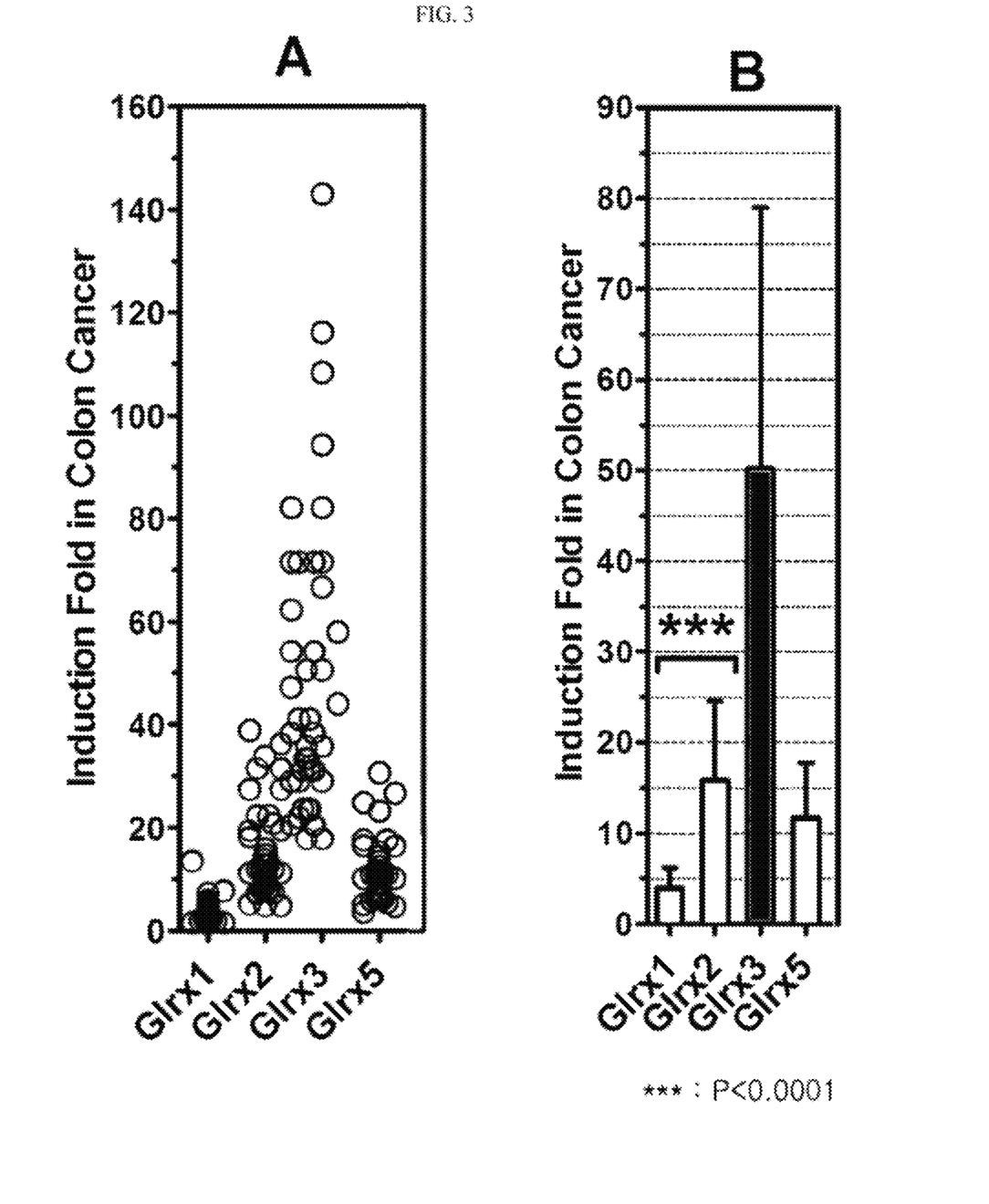
FIGS. 3A and 3B are of graphs showing mRNA levels of glutaredoxin 1, 2, 3 and 5 in colorectal cancer as measured by qRT-PCR using HCRT II arrays, and magnitudes of the induction fold obtained therefrom.

The results are given in FIGS. 3A and 3B.

As is apparent from the data of FIGS. 3A and 3B, the mRNA level of glutaredoxin 3 was the highest in colorectal cancer tissues (induction fold, 50.2 ±28.8).

1-4 . Preferential Expression of Glutaredoxin 3 mRNA in Lung Cancer and Colorectal Cancer The mRNA expression levels of glutaredoxin 3 in various cancer tissues (bladder, breast, colon, kidney, liver, lung, lymphoma, ovary, prostate and thyroid) were measured using qRT-PCR arrays.

Figure 4:
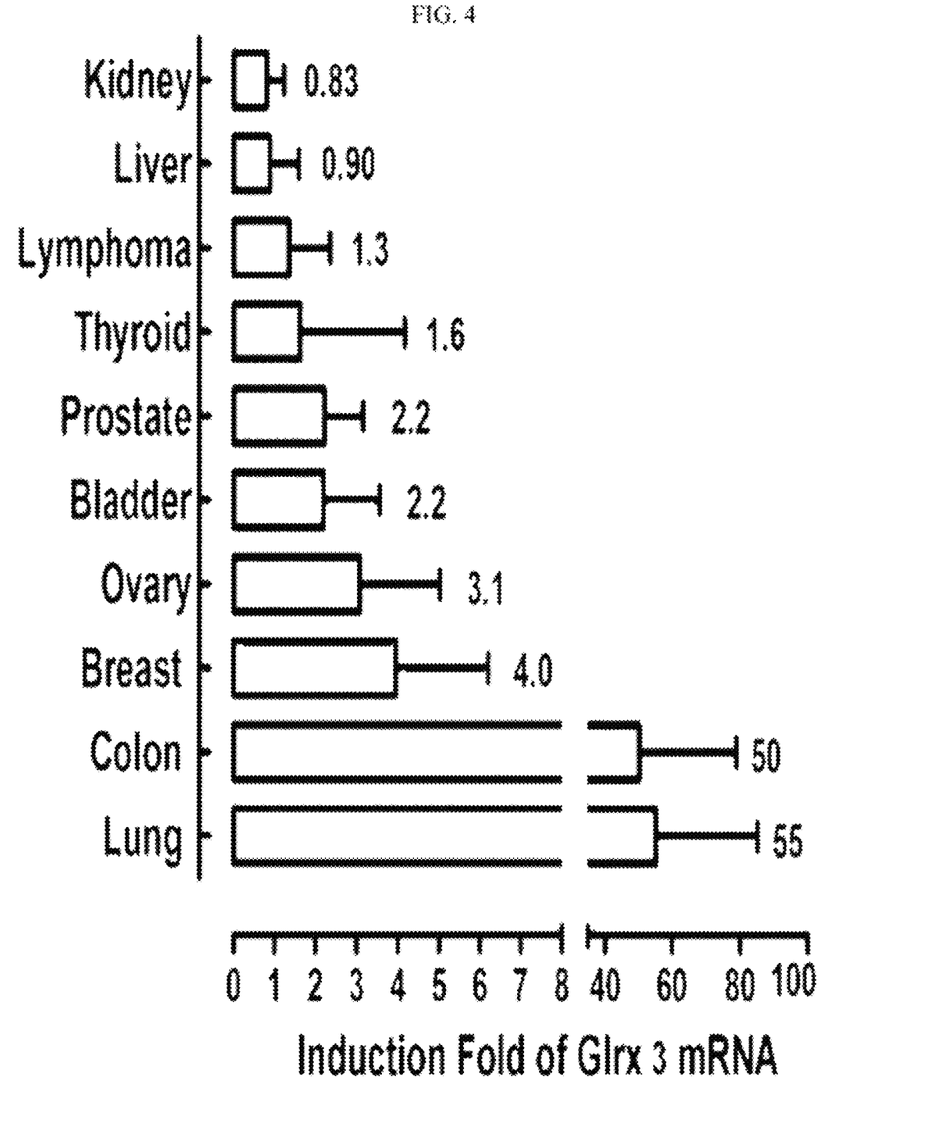
FIG. 4 is a diagram showing magnitudes of induction fold obtained from the measurements of mRNA levels of glutaredoxin 1, 2, 3 and 5 in various cancerous tissues (bladder, breast, colon, kidney, liver, lung, lymphoma, ovary, prostate and thyroid) as determined by qRT-PCR.

The results are given in FIG. 4.

As can be seen in FIG. 4, glutaredoxin 3 was preferentially induced in lung cancer and colorectal cancer (lung colon≥breast>ovary>bladder≥prostate), but little or not expressed in thyroid cancer, lymphoma, liver cancer and kidney cancer.

1-5 . Correlation between Glutaredoxin 3 and Survivin mRNA Expression in Lung Cancer The HLRT II array (qRT-PCR) was used to determine the mRNA transcript levels of glutaredoxin 1 glutaredoxin 3 and survivin. Survivin is an inhibitor against apoptosis which plays a crucial role in cell survival, allowing for continued proliferation. Survivin has been detected in a wide range of cancers including lung cancer. In lung cancer, the expression of surviving protein is reported to positively correlate with the tumor stage.

Figure 5:
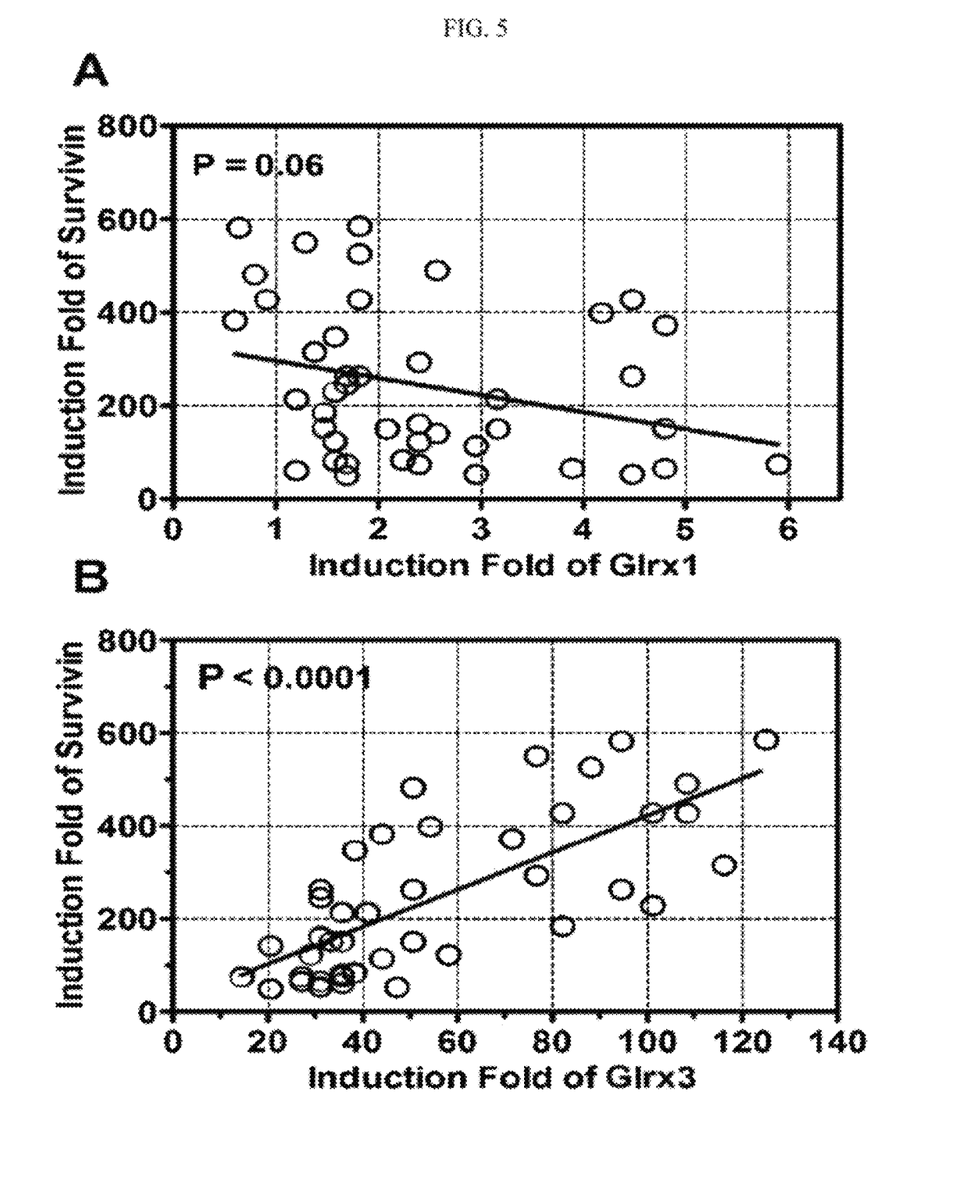
FIGS. 5A and 5B are of graphs showing the correlation between the mRNA expression of glutaredoxin 1 (FIG. 5A) or glutaredoxin 3 (FIG. 5B) and survivin in lung cancer.

The results are given in FIGS. 5A and 5B.

As can be seen in FIGS. 5A and 5B, the expression of glutaredoxin 1 mRNA appeared to have weak or negative correlation with the induction of survivin mRNA (A), whereas the expression of glutaredoxin 3 mRNA was significantly correlated with the induction of survivin mRNA in lung cancer (B).

EXAMPLE 2

Western Blot Analysis

To examine the expression level of glutaredoxin 3 in human lung cancer and colorectal cancer tissues with Western blotting analysis, the following experiment was conducted.

Total membrane and soluble proteins from clinically defined human cancer and normal tissues were obtained from Capital Biosciences (Gaithersburg, Md., USA). Proteins from different individuals and matched paired individuals (normal tissue and primary cancers; primary and metastatic cancers) were used for immunological analysis. The clinical and pathological traits of the cancers are summarized in Tables 3~5 below.

Western blotting analysis was performed using the Amersham ECL Western blotting system (GE Healthcare, Chalfont St. Giles, United Kingdom). Anti-Glrx3 rabbit polyclonal antibody that has cross-reactivity with the corresponding human Glrx3 was purchased from AbFrontier (Seoul, Korea). Samples were fractionated by electrophoresis on a 4~20% gradient SDS-PAGE (GenScript Corp, Piscataway, N.J., USA) and transferred onto PVDF (polyvinylidene difluoride) membranes (Millipore, Billerica, Mass., USA). The membranes were blocked and incubated at room temperature for 2 hrs with antibody (1:1000 by volume) in PBS containing 0.1% Tween 20 . After washing many times, the membranes were incubated with polyclonal goat anti-rabbit IgG antibody (1:2000 by volume) conjugated with HRP (horseradish peroxidase). The membranes were washed in PBS, and the chemiluminescent substrate was added. The membranes were stripped and stained with Coomassie Blue R-250 for verification of the loading sample.

TABLE 3

| Tissue | Age/Gender | Diagnosis |
|---|---|---|
| Brain | 26/Male | Normal |
|  | 40/Male | Astrocytoma |
| Breast | 82/Female | Normal |
|  | 47/Female | Medullary carcinoma, well differentiated |
| Colon | 60/Female | Normal |
|  | 48/Male | Adenocarcinoma, well differentiated |
| Kidney | 83/Female | Normal |
|  | 43/Female | Granular cell carcinoma |
| Liver | 30/Male | Normal |
|  | 65/Male | Hepatic cellular carcinoma |
| Lung | 24/Female | Normal |
|  | 72/Male | Squamous cell carcinoma |
| Ovary | 74/Female | Normal |
|  | 51/Female | Cystadenoma |
| Pancreas | 78/Female | Normal |
|  | 61/Male | Adenocarcinoma, moderately differentiated |
| Prostate | 26/Male | Normal |
|  | 79/Male | Adenocarcinoma |
| Spleen | 30/Male | Normal |
|  | 40/Male | Capillary Hemangioma |
| Stomach | 47/Male | Normal |
|  | 65/Male | Adenocarcinoma |
| Testicles | 25/Male | Normal |
|  | 30/Male | Normal (Seminoma) |
| Thyroid | 74/Female | Normal |
|  | 20/Male | Adenocarcinoma, papillary, well differentiated |
| Uterine | 43/Female | Normal |
|  | 43/Female | Adenocarcinoma |

TABLE 4

| Sample | | Appearance | Age/Gender | Diagnosis |
|---|---|---|---|---|
| Breast | 1N | Normal | 70/Female | Normal |
|  | 1P | Primary tumor |  | Invasive Ductal Carcinoma |
|  | 2P | Primary tumor | 59/Female | Breast cancer |
|  | 2M | Metastatic tumor |  | Breast tumor metastasized to lung |
| Colon | 1N | Normal | 62/Female | Normal |
|  | 1P | Primary tumor |  | Adenocarcinoma |
|  | 2P | Primary tumor | 66/Female | Adenocarcinoma |
|  | 2M | Metastatic tumor |  | Colon tumor metastasized to lymph node |
| Lung | 1N | Normal | 46/Male | Normal |
|  | 1P | Primary tumor |  | Squamous cell carcinoma |
|  | 2P | Primary tumor | 75/Male | Squamous cell carcinoma |
|  | 2M | Metastatic tumor |  | Lung tumor metastasized to lymph node |

TABLE 5

| | Sample | Age/Gender | Diagnosis |
|---|---|---|---|
| Breast | N1~N3 | 56/Female, 64/Female, 76/Female | Normal |
|  | C1 | 50/Female | Invasive Ductal Carcinoma |
|  | C2 | 42/Female | Adenocarcinoma, moderately differentiated |
|  | C3 | 42/Female | Fibroadenoma |
|  | C4 | 40/Female | Invasive Lobular carcinoma |
| Colon | N1~N3 | 26/Female, 28/Male, 71/Male | Normal |
|  | C1 | 56/Male | Adenocarcinoma, moderately differentiated |
|  | C2 | 57/Male | Adenocarcinoma, moderately differentiated |
|  | C3 | 68/Female | Adenocarcinoma, mucinous, poorly differentiated |
|  | C4 | 75/Male | Adenocarcinoma, moderately differentiated |
| Lung | N1, N2 | 66/Male, 76/Female | Normal |
|  | C1 | 33/Male | Squamous Cell Carcinoma, well differentiated |
|  | C2 | 51/Female | Adenocarcinoma, moderately differentiated |
|  | C3 | 58/Male | Squamous Cell Carcinoma, well differentiated |
|  | C4 | 61/Male | Adenocarcinoma |

Figure 6:
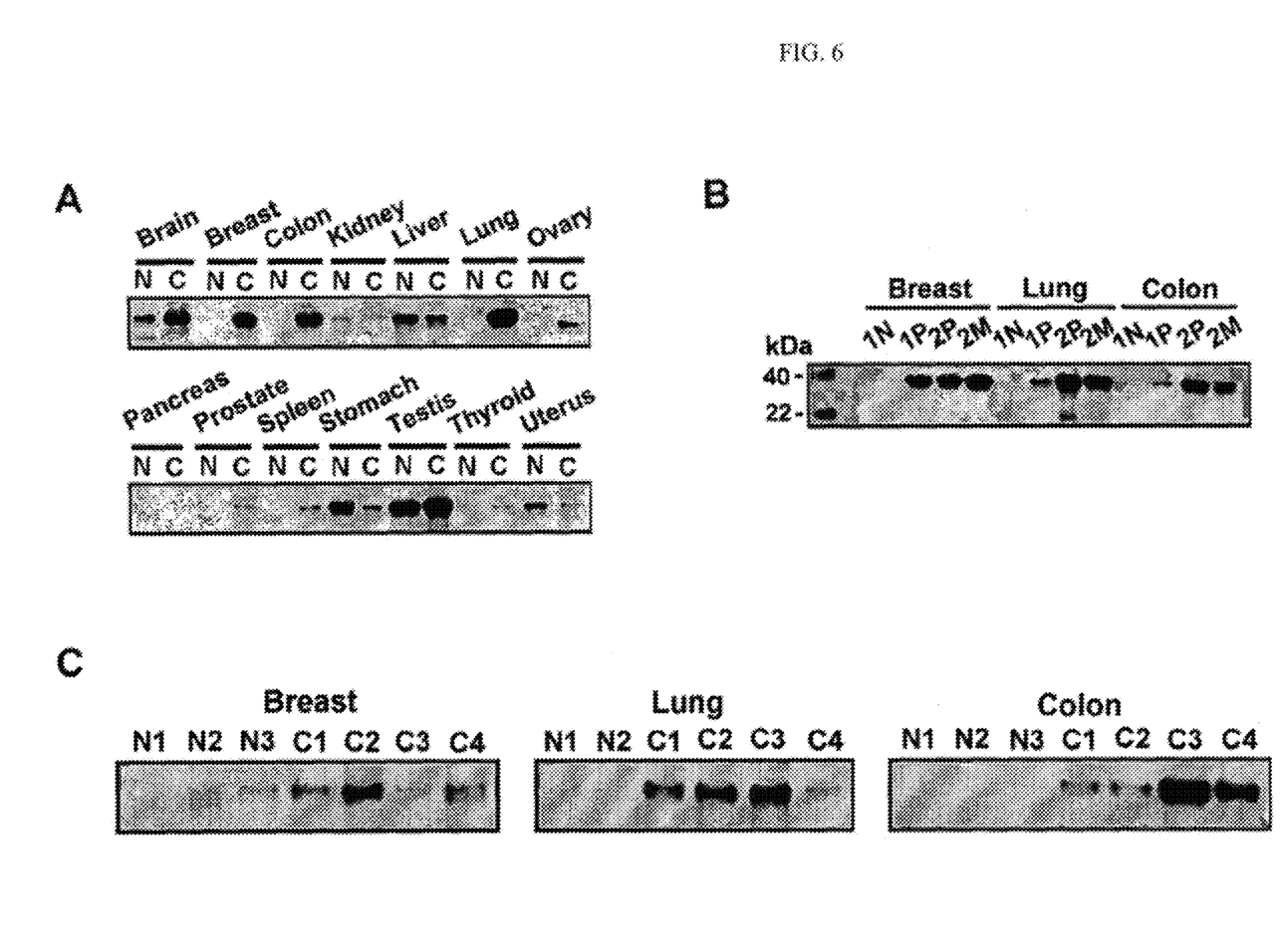
FIG. 6 shows the expression levels of glutaredoxin 3 in normal human tissue and corresponding cancer tissues (A), in paired sets of breast, lung and colon tissues (paired normal and primary cancer from the same individual; paired primary and metastatic cancer from the same individual) (B), and in human normal tissues and cancerous tissues (breast, lung and colon) (C), as measured by Western blotting assay.

In FIG. 6, Western blot analysis results are given of glutaredoxin 3 protein expression in human normal tissue and the corresponding cancerous tissue (A), in paired sets of breast, lung and colon tissues (paired normal and primary cancer from the same individual; paired primary and metastatic cancer from the same individual) (B), and in human normal tissues and cancerous tissues (breast, lung and colon) (C).

As is apparent from the data of FIG. 6, glutaredoxin 3 was expressed at high levels in cancerous tissues of the breast, the lung and the colon, with a peak in lung cancer. In contrast, the protein was not expressed in normal breast, lung and colon tissues (A). When it comes to a comparison between paired sets of breast, lung and colon tissues (paired normal and primary cancer from the same individual; paired primary and metastatic cancer from the same individual), glutaredoxin 3 was overexpressed in cancerous tissues (B). In addition, glutaredoxin 3 was preferentially expressed in cancerous tissues (breast, lung and colon), particularly more preferentially in lung and colon cancer tissues, over normal human tissues (C).

Industrial Applicability

Being preferentially overexpressed in cancerous tissues of the lung and the colon, glutaredoxin 3 can be used as a diagnostic biomarker which allows for an accurate diagnosis and prognosis of lung cancer and colorectal cancer to be made.

The invention claimed is:

1. A method of diagnosis or prognosis of lung cancer in a subject, the method comprising:
providing a tissue of the subject;
processing the tissue to isolate mRNAs contained in the tissue;
generating cDNAs complementary to the isolated mRNAs;
mixing the cDNAs with a forward rimer consisting of SEQ ID NO: 5 and a reverse primer consisting of SEQ ID NO: 6, which to provide a mixture;
performing a qRT-PCR using the mixture and a PCR composition to amplify one or more cDNA sequences recognized by the forward and reverse primers;
determining an expression level of glutaredoxin 3 in the tissue based on results of the qRT-PCR; and
diagnosing or prognosing lung cancer when the expression level is higher than a reference value.

2. The method according to claim 1, further comprising:
providing a control tissue; and
processing the tissue to isolate mRNAs contained in the control tissue;
generating cDNAs complementary to the isolated mRNAs;
mixing the cDNAs with a forward primer consisting of SEQ ID NO: 5 and a reverse primer consisting of SEQ ID NO: 6, which to provide a mixture;
performing a qRT-PCR using the mixture and a PCR composition to amplify one or more cDNA sequences recognized by the forward and reverse primers;
determining an expression level of glutaredoxin 3 in the control tissue;
wherein the expression level glutaredoxin 3 in the control tissue provide the reference value.

3. The method according to claim 1, wherein the reference value is a predetermined value.

4. A method of diagnosis or prognosis of colorectal cancer in a subject, the method comprising:
providing a tissue of the subject;
processing the tissue to isolate mRNAs contained in the tissue;
generating cDNAs complementary to the isolated mRNAs;
mixing the cDNAs with a forward primer consisting of SEQ ID NO: 5 and a reverse primer consisting of SEQ ID NO: 6, which to provide a mixture;
performing a qRT-PCR using the mixture and a PCR composition to amplify one or more cDNA sequences recognized by the forward and reverse primers;
determining an expression level of glutaredoxin 3 in the tissue based on results of the qRT-PCR; and
diagnosing or prognosing colorectal cancer when the expression level is higher than a reference value.

5. The method according to claim 4, further comprising:
providing a control tissue; and
processing the tissue to isolate mRNAs contained in the control tissue;
generating cDNAs complementary to the isolated mRNAs;
mixing the cDNAs with a forward primer consisting of SEQ ID NO: 5 and a reverse primer consisting of SEQ ID NO: 6, which to provide a mixture;
performing a qRT-PCR using the mixture and a PCR composition to amplify one or more cDNA sequences recognized by the forward and reverse primers;
determining an expression level of glutaredoxin 3 in the control tissue;
wherein the determined expression level glutaredoxin 3 in the control tissue provides the reference value.

6. The method according to claim 4, wherein the reference value is a predetermined value.

* * * * *